(12) United States Patent
Hermann et al.

(10) Patent No.: US 9,951,006 B2
(45) Date of Patent: Apr. 24, 2018

(54) METHOD FOR PRODUCING POWDERED LAUROYL PEROXIDE

(71) Applicant: United Initiators GmbH, Pullach (DE)

(72) Inventors: Dominik Hermann, Dachau (DE); Iris Nagl, München (DE); Hanno Wolf, Ottobrunn (DE)

(73) Assignee: United Initiators GmbH, Pullach (DE)

( * ) Notice: Subject to any disclaimer, the term of this patent is extended or adjusted under 35 U.S.C. 154(b) by 0 days.

(21) Appl. No.: 15/531,546

(22) PCT Filed: Nov. 26, 2015

(86) PCT No.: PCT/EP2015/077789
§ 371 (c)(1),
(2) Date: Nov. 6, 2017

(87) PCT Pub. No.: WO2016/083514
PCT Pub. Date: Jun. 2, 2016

(65) Prior Publication Data
US 2018/0044289 A1    Feb. 15, 2018

(30) Foreign Application Priority Data
Nov. 28, 2014   (EP) ..................................... 14195444

(51) Int. Cl.
*C07C 407/00* (2006.01)
*C07C 409/00* (2006.01)
*C07C 409/34* (2006.01)
*B01J 19/00* (2006.01)
*C07B 41/14* (2006.01)

(52) U.S. Cl.
CPC ....... *C07C 407/006* (2013.01); *B01J 19/0013* (2013.01); *B01J 19/0066* (2013.01); *C07B 41/14* (2013.01); *C07C 409/34* (2013.01); *B01J 2219/00029* (2013.01)

(58) Field of Classification Search
CPC .... C07C 407/006; C07C 409/34; C07B 41/14
USPC ......................................................... 568/559
See application file for complete search history.

(56) References Cited

FOREIGN PATENT DOCUMENTS

| | | |
|---|---|---|
| DE | 38 072 A | 6/1965 |
| DE | 17 68 199 A1 | 1/1972 |
| GB | 950978 A | 3/1964 |
| GB | 1135372 A | 12/1968 |
| GB | 1 198 424 A | 7/1970 |
| GB | 2054583 A | 2/1981 |
| JP | S49 36593 A | 4/1974 |

*Primary Examiner* — Sikarl A Witherspoon
(74) *Attorney, Agent, or Firm* — Withers & Keys, LLC

(57) ABSTRACT

The present application relates to a method for producing powdered lauroyl peroxide which is characterized in that a reaction mixture is used which comprises water, lauric acid chloride, hydrogen peroxide, an inorganic base and an alkane.

20 Claims, 2 Drawing Sheets

Figure 1:
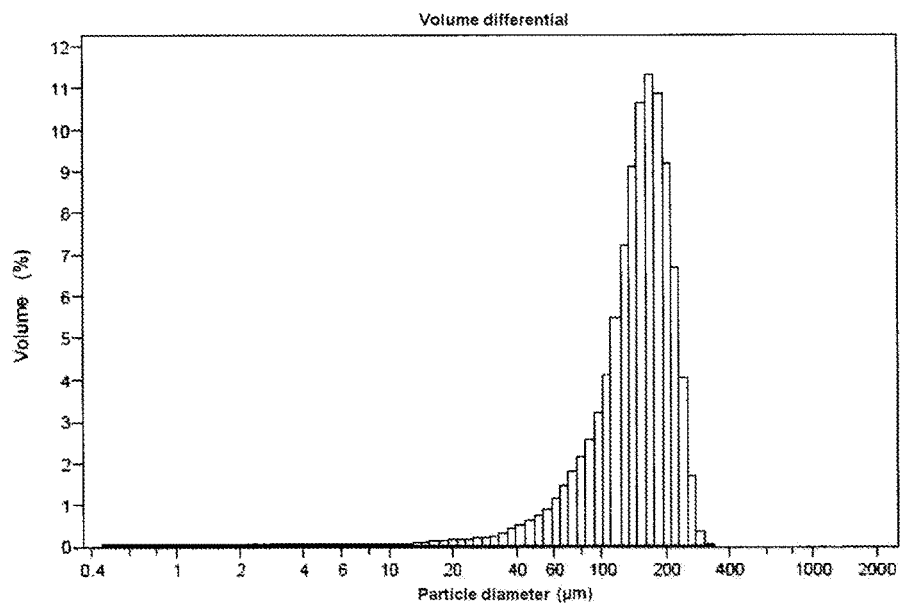

| Volume statistics (arithmetic) | | | | | |
|---|---|---|---|---|---|
| Calculation from 0.375 µm to 2000 µm | | | | | |
| Volume: | 100% | | | | |
| Mean value: | 398.4 µm | | SD: | 329.0 µm | |
| Median value: | 359.7 µm | | Variance: | 108.3e3 µm² | |
| Mean/median value: | 1.108 | | CV: | 82.6% | |
| Maximum: | 684.2 µm | | Skewness: | 0.449 right-skewed | |
| | | | Kurtosis: | -0.957 Platykurtic | |
| <10% | <25% | <50% | <75% | <90% | <95% |
| 28.68 µm | 73.04 µm | 359.7 µm | 665.5 µm | 855.9 µm | 965.6 µm |

METHOD FOR PRODUCING POWDERED LAUROYL PEROXIDE

This application is being filed as the national stage patent application of PCT International Patent Application No. PCT/EP2015/077789, filed on 26 Nov. 2015, and claiming priority to European Patent Application Serial No. 14195444.6, filed on 28 Nov. 2014, and entitled "METHOD FOR PRODUCING POWDERED LAUROYL PEROXIDE," the contents of both of which is incorporated herein by reference in its entirety.

The present application relates to a method for producing powdered lauroyl peroxide which is characterised in that a reaction mixture is used which comprises water, lauric acid chloride, hydrogen peroxide, an inorganic base and an alkane.

Lauroyl peroxide (also known as di(dodecanoyl) peroxide or dilauroyl peroxide) is an initiator used for polymerisation reactions which has a wide range of uses. It can exist, for example, as a colourless, coarse powder which is insoluble in water but soluble in oils and many organic solvents. The melting point thereof is in the range of from approximately 48° C. to 54° C. In general, organic peroxides are thermally unstable compounds which decompose exothermically, by cleavage of the peroxidic oxygen-oxygen bond. Lauroyl peroxide is therefore highly reactive. The critical temperature of this compound, at which temperature self-accelerating decomposition (SADT) begins, also lies in the temperature range of the melting point.

Lauroyl peroxide can also be produced from lauric acid chloride and hydrogen peroxide in the presence of aqueous solutions of inorganic bases. The synthesis, processing and formulations of lauroyl peroxide are described in numerous publications.

DD 38072 describes the continuous production of lauroyl peroxide from lauric acid chloride and hydrogen peroxide in a series of stirred-tank reactors at 60° C. For the purpose of processing, the molten lauroyl peroxide is allowed to flow in cold water and the solidified product is centrifuged off.

The likewise continuous process according to DE 29 28 020 A1 operates in synthesis at from 0 to 20° C. For the purpose of processing, the lauroyl peroxide has to be heated above the melting point thereof. The melt can be separated off on a separator.

DE 1 192 181 discloses a method for production in the solvent heptane which operates at a synthesis temperature of from 40 to 65° C. After purification of the reaction solution, the lauroyl peroxide has to be crystallised out by cooling the solution to 0° C.

Lauroyl peroxide is commercially available in the form of flakes, pastes or as an aqueous suspension. For certain applications, however, it is necessary to provide lauroyl peroxide in the form of a fine powder. A powder having a small particle size thus permits particularly good solubility in solvents, resins or monomers for example. In order to process a lauroyl peroxide crude product, which is obtained according to production methods known from the prior art, into a powder, in general at least one additional method step would be necessary, while pulverising the crude product. Optionally, a further method step would also have to precede this step, in which synthesised lauroyl peroxide is first melted, purified and then solidified again. However, since heating lauroyl peroxide above the melting point thereof, as described above, entails a certain safety risk, this places further demands on the mechanical equipment and the execution of the method, which in turn is associated with additional costs. In this context, it would be desirable to render obsolete method steps of this kind involving melting and pulverising a lauroyl peroxide crude product.

The object of the present invention was therefore that of providing a method for producing lauroyl peroxide, by means of which lauroyl peroxide is obtained directly, i.e. without additional method steps for melting and pulverising the crude product, as a very fine, homogeneous powder. Furthermore, a method of this kind should be simple to carry out and safe.

In the context of the present invention, it was found that it is possible to carry out the method in this way when, during production, an alkane is added to a mixture of lauric acid chloride, hydrogen peroxide and an inorganic base. Surprisingly, the lauroyl peroxide powder thus obtained is also distinguished by a very high level of purity.

One aspect of the present invention therefore relates to a method for producing powdered lauroyl peroxide which is characterised in that a reaction mixture is used which comprises water, lauric acid chloride, hydrogen peroxide, an inorganic base and an alkane.

The production of lauroyl peroxide according to the invention is preferably carried out in the aqueous phase.

The method is preferably carried out at a predetermined temperature in the range of from approximately 5° C. to approximately 40° C., more preferably in the range of from approximately 10° C. to approximately 30° C., more preferably in the range of from approximately 15° C. to approximately 20° C.

The alkane used can be selected from the group consisting of straight-chain, branched-chain and cyclic alkanes and mixtures thereof. $C_{5-12}$-alkanes such as pentane, hexane, heptane, octane, nonane, decane, undecane or dodecane and their isomers, or mixtures thereof such as petroleum ether are preferred in this case. More preferably hexane, in particular isohexane, is used.

The inorganic base is preferably used as an aqueous solution of an inorganic base. A lye such as caustic soda lye or potash lye for example can be used as the aqueous solution of an inorganic base. Aqueous solutions of sodium hydroxide, potassium hydroxide, sodium carbonate, potassium carbonate or calcium hydroxide and/or mixtures thereof can be used for example. Preferably, aqueous solutions of sodium hydroxide, potassium hydroxide or mixtures thereof are used.

For example, an aqueous solution comprising between 1 wt. % and 50 wt. % of an inorganic base can be used as the aqueous solution of an inorganic base or of the abovementioned mixtures thereof. An aqueous solution can be used, for example, which comprises 10 wt. %, 15 wt. %, 20 wt. %, 25 wt. %, 30 wt. %, 40 wt. % or 50 wt. % of an inorganic base. Preferably, 25%-caustic soda lye or potash lye is used, i.e. an aqueous solution comprising 25 wt. % sodium hydroxide or potassium hydroxide.

The pH of the reaction mixture is in the range of from pH 9 to pH 14, preferably approximately pH 11 to approximately pH 14, more preferably approximately pH 12 to approximately pH 14, yet more preferably approximately pH 13 to approximately pH 14, most preferably approximately pH 14.

Hydrogen peroxide is preferably used in the form of an aqueous solution. In this case, a solution of any concentration can be used. The aqueous hydrogen peroxide solution can comprise, for example, approximately 5 wt. %, approximately 10 wt. %, approximately 20 wt. %, approximately 30 wt. %, approximately 40 wt. %, approximately 50 wt. %, approximately 60 wt. %, approximately 70 wt. % or approximately 80 wt. % hydrogen peroxide.

The molar excess of hydrogen peroxide above the theoretically required amount in the reaction mixture should be from approximately 30% to approximately 80%, preferably from approximately 50% to approximately 60%. The term "theoretically required amount" regarding hydrogen peroxide denotes the amount of hydrogen peroxide which should be used in order to provide one hydrogen peroxide substance amount equivalent for every two lauric acid chloride substance amount equivalents in the reaction mixture. However, for the ratio of hydrogen peroxide used to lauric acid chloride used, it has been found to be advantageous to use hydrogen peroxide in the above-mentioned excess relative to the theoretically required amount in order to achieve an improved yield of lauroyl peroxide.

The hydrogen peroxide concentration in the reaction mixture at the start of the reaction can be from 0.5 wt. % to 10 wt. %, preferably from 1 wt. % to 5 wt. %, more preferably from 2 wt. % to 3 wt. %.

At least one inorganic base substance amount equivalent in each case should be used per lauric acid chloride substance amount equivalent in the reaction mixture. However, it is preferred to use a certain excess of inorganic base compared thereto, it being intended for the molar excess above the theoretically required amount in the reaction mixture to be the same as for hydrogen peroxide.

The mass ratio of alkane to lauric acid chloride in the reaction mixture can be in the range of from approximately 1:10 to approximately 1:1, preferably approximately from 1:5 to approximately 1:1, more preferably from approximately 1:4.5 to approximately 1:2, yet more preferably said ratio is approximately 1:4. In principle, alkane can, however, also be used in excess in this mass ratio.

The mass ratio of aqueous phase to alkane in the reaction mixture can be in the range of from approximately 100:10 to approximately 100:1, preferably in the range of from 100:8 to 100:2, more preferably, said ratio is approximately 100:4, the aqueous phase comprising water, hydrogen peroxide and an inorganic base.

The reaction mixture can contain further components. Said further components can be selected for example from the group consisting of stabilisers for hydrogen peroxide, surfactants, alcohols and combinations thereof. Complexing agents can be used as stabilisers for hydrogen peroxide, ethylenediaminetetraacetic acid and/or salts thereof is/are preferably used.

The method execution according to the invention makes the following synthesis mechanism possible. Hydrogen peroxide and caustic soda lye react in the aqueous phase to form sodium peroxide. The added alkane is not miscible with water and provides an organic phase in the reaction mixture which preferably forms a significantly smaller proportion of the reaction mixture than does the aqueous phase. The additionally added lauric acid chloride firstly dissolves in this organic phase. Subsequently, in the manner of the Schotten-Baumann reaction, it reacts quickly at the interface to the aqueous phase with sodium peroxide to form lauroyl peroxide. In the case of the synthesis temperatures used according to the present invention, said lauroyl peroxide is in general not soluble in alkane and crystallises, with the result that a suspension of lauroyl peroxide in the aqueous phase is obtained. In contrast to synthesis reactions known up to now, powdered lauroyl peroxide is obtained directly and is additionally distinguished by the advantageous properties described herein. Of course, the method according to the invention is not necessarily limited to the synthesis mechanism described.

The method according to the invention can be carried out as a batch process or as a continuous process, a batch process being preferred.

The method according to the invention can be carried out in any suitable reactor. Preferably, a stirred-tank reactor is used for carrying out the method according to the invention.

The method according to the invention preferably comprises the following steps:
i) providing an aqueous solution comprising hydrogen peroxide and an inorganic base;
ii) adding an alkane;
iii) adding lauric acid chloride in a temperature-controlled manner while stirring;
iv) continuing the stirring in a temperature-controlled manner;
v) filtering the resulting precipitate, preferably using a Nutsche filter;
vi) washing the precipitate, preferably using water;
vii) optionally drying the precipitate.

Within the meaning of this invention, a temperature-controlled step means a method step during which a predetermined temperature in the range of from approximately 5° C. to less than approximately 40° C., preferably in the range of from approximately 10° C. to approximately 30° C., more preferably in the range of from approximately 15° C. to approximately 20° C., is maintained.

According to the invention, an aqueous solution comprising hydrogen peroxide, an inorganic base and an alkane can be provided and cooled to a predetermined temperature in the range of from approximately 5° C. to less than approximately 40° C., preferably in the range of from approximately 10° C. to approximately 30° C., more preferably in the range of from approximately 15° C. to approximately 20° C. The cooling occurs by means of jacket cooling or coil cooling for example or, in the case of a tubular reactor, by means of a heat exchanger. Subsequently, lauric acid chloride can be added in a temperature-controlled manner. The reaction mixture is stirred for example using a propeller stirrer having stirring speeds in the range of from approximately 1000 to approximately 3000 rpm.

Instead of sequentially adding the alkane and lauric acid chloride in two separate steps, ii) and iii), according to the invention the alkane, or at least some of the alkane, and the lauric acid chloride can also be mixed together in advance and subsequently added to the aqueous solution or to the aqueous solution already comprising some of the alkane. Consequently, in the above scheme, steps ii) and iii) can also be combined either partially or completely.

Lauric acid chloride or a mixture comprising alkane and lauric acid chloride is preferably added dropwise in a temperature-controlled manner. This addition preferably occurs during a period of from approximately 10 minutes to 30 minutes, while stirring. Once all the lauric acid chloride has been added, the stirring is continued, preferably for a period of from approximately 10 minutes to approximately 30 minutes.

During the addition of lauric acid chloride or of a mixture comprising alkane and lauric acid chloride, the cooling is controlled such that the temperature of the reaction mixture does not exceed the above-defined desired temperature range. It is preferred for the desired temperature range to be maintained by means of cooling, at least during steps ii) to iv). Optionally, in addition one or more or all of steps i) and v) to vii) can also occur at the same temperature.

The precipitate obtained following step iv) is powdered lauroyl peroxide which can be processed without first separating the organic and aqueous phase. Separation of the lauroyl peroxide precipitate from the reaction mixture can be achieved by means of any method, for example using filters, Nutsche filters, belt filters or centrifuges. When using a Nutsche filter, the filter cake can for example be washed with water directly on the Nutsche filter, or can be separately mixed with water again and re-filtered out. A lauroyl peroxide powder obtained in this way, which is still damp from water, can have a content of approximately 75 wt. % and can subsequently be dried by means of air or a vacuum. The powdered lauroyl peroxide obtained is present in a very fine and homogeneous form and has a high level of purity.

In methods for producing lauroyl peroxide known from the prior art, it is often necessary to melt the lauroyl peroxide crude product, for example for purification purposes. In contrast, it is essential to the invention that neither the reaction mixture nor the lauroyl peroxide powder obtained is heated, at any time during the method, to a temperature which is above the melting point of lauroyl peroxide. This ensures both increased safety of the method and permits simpler and more cost-effective implementation.

A further aspect of the present invention relates to a powdered lauroyl peroxide produced by the method according to the invention. As will be explained in the following, this product is distinguished in that it is in the form of a very fine and homogeneous powder and in addition has a very high level of purity. Lauroyl peroxide is obtained in this form in the method according to the invention without the need for further method steps, such as pulverising.

The lauroyl peroxide produced in accordance with the method according to the invention has a $d_{90}$ value in the range of from 50 µm to 500 µm, preferably in the range of from 50 µm to 400 µm, and a $d_{50}$ value in the range of from 10 µm to 300 µm, preferably in the range of from 10 µm to 250 µm. $d_{50}$ and $d_{90}$ values are defined by 50% or 90%, respectively, of the particles contained in a random sample having a smaller particle diameter than the respective $d_{50}$ or $d_{90}$ value of the sample. For the lauroyl peroxide produced in accordance with the method according to the invention, the distribution spectrum of the particle size has an individual, very homogeneous band.

The powdered lauroyl peroxide produced in accordance with the method according to the invention is distinguished by a very high level of purity immediately after being washed with water in step vi). Said powder thus has a dry content of over 98.5 wt. %, preferably over 99.0 wt. %, more preferably over 99.2 wt. %, yet more preferably over 99.5 wt. % lauroyl peroxide. The dry content of lauric per-acid is less than 0.1 wt. %, preferably even less than 0.05 wt. %, more preferably less than 0.02 wt. %. The residual chlorine content is less than 200 ppm, preferably less than 100 ppm, more preferably less than 70 ppm.

The powdered lauroyl peroxide produced in accordance with the method according to the invention is obtained in a yield of equal to or over 90%, preferably equal to or over 95%, more preferably equal to or over 96%, yet more preferably equal to or over 98%. The yield refers to the substance amount of lauroyl peroxide obtained based on the substance amount of lauric acid chloride used, one equivalent of lauroyl peroxide theoretically being produced from two equivalents of lauric acid chloride.

A further aspect of the present invention relates to the use of alkanes, particularly preferably isohexane, when producing lauroyl peroxide in the aqueous phase at synthesis temperatures in the range of from approximately 5° C. to less than approximately 40° C., as described herein.

FIGURES

Figure 2:
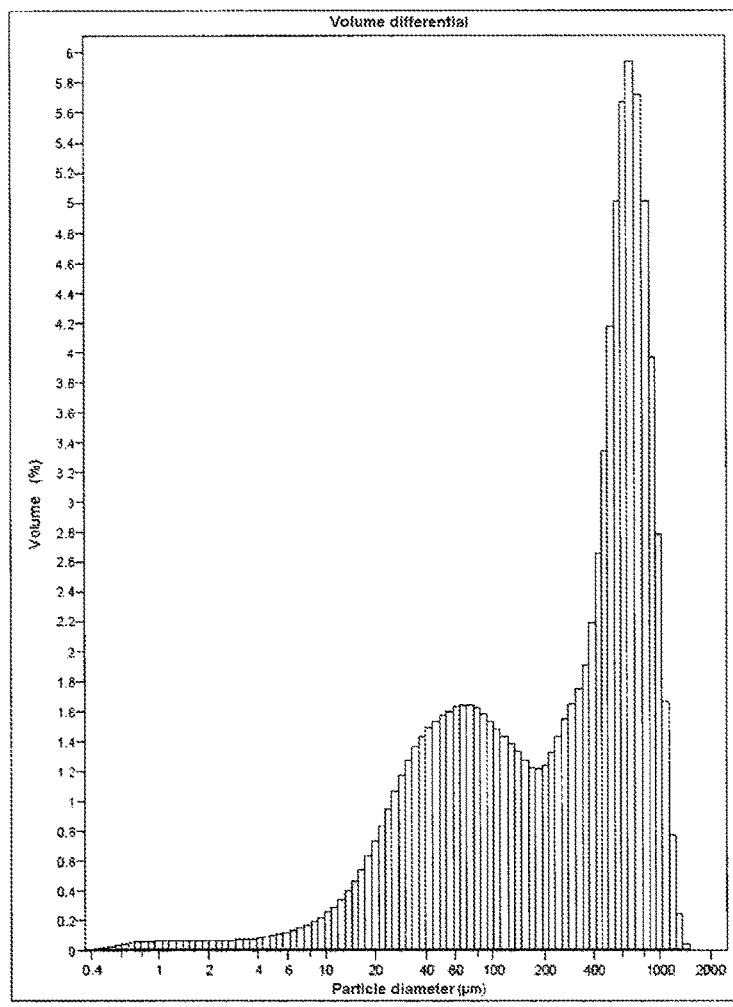

FIG. 1 shows the particle size distribution of lauroyl peroxide produced according to the invention, FIG. 2 shows the particle size distribution of lauroyl peroxide produced according to the prior art.

EXAMPLES

Example 1: Production of Powdered Lauroyl Peroxide 1250 g water, 42 g (0.86 mol) hydrogen peroxide 70%, 252 g (1.58 mol) caustic soda lye 25% and 60 g isohexane are provided and cooled to 16° C. 240 g (1.10 mol) lauric acid chloride are added dropwise, over 20 minutes while cooling, at temperatures of from 16 to 18° C. Following the addition, the reaction mixture is stirred for a further 20 minutes at the same temperature. Said mixture is filtered using a Nutsche filter and the solid matter obtained is repeatedly washed using a total of 4 liters of water. 291 g of product damp from water is obtained having a content of 75%, which corresponds to a yield of 98%. After drying in air or in a vacuum, the lauroyl peroxide content was 99.1%. The chlorine content in the product is 60 ppm, the lauric per-acid content is 0.01%.

The particle size distribution is very homogeneous without any further pulverisation and has a $d_{50}$ value of 153 µm and a $d_{90}$ value of 222 µm. The spread is shown in FIG. 1. A spread of a commercially available lauroyl peroxide powder has been recorded for the purpose of comparison (FIG. 2). Said powder has a $d_{50}$ value of 360 µm and a $d_{90}$ value of 856 µm.

Example 2: Use of Lauroyl Peroxide in Resin Curing

Lauroyl peroxide (LP) is used not only in PVC production, but also in resin curing for example. For this purpose, said lauroyl peroxide has to first be dissolved in the polystyrene resin. Comparative dissolution trials were carried out for commercially available LP flakes and LP powder according to the invention. In the process it was found that, as expected, the LP powder dissolved more quickly than the flakes.

TABLE 1

Dissolution speed of LP in 20 g styrene, while stirring

| | Amount in g | Dissolution time in min |
|---|---|---|
| LP flakes° | 9.5 | 8 |
| Dry LP | 9.5 | 6 |
| LP-75-W * | 11.0 | 6 |

* powder, damp from water, having 75% LP content
° not according to the invention During a curing trial, the gel time $t_{gel}$, the maximum temperature $T_{max}$ reached in the process, and the time $t_{max}$ until this maximum temperature was reached, were determined:

Curing: in accordance with DIN 16945 in a test tube at 80° C.

Resin: Palatal P4

Filler: aluminium trihydroxide (40 parts to 100 parts resin)

| | Peroxide amount | $t_{gel}$ in min | $t_{max}$ in min | $T_{max}$ in °C |
|---|---|---|---|---|
| LP flakes° | 1.0% | 27.9 | 31.6 | 155 |
| Dry LP | 1.0% | 24.9 | 27.8 | 163 |
| LP-75-W | 1.3% | 25.5 | 28.2 | 165 |

°not according to the invention

It can be seen that the times $t_{gel}$ and $t_{max}$ are shorter and $T_{max}$ is longer. Accordingly, the LP powder is more active than the LP flakes.

The invention claimed is:

1. Method for producing powdered lauroyl peroxide having a particle size according to the $d_{90}$ value of from 50 μm to 400 μm, wherein a reaction mixture is used which comprises water, lauric acid chloride, hydrogen peroxide, an inorganic base and an alkane, and the method is carried out at a predetermined temperature in the range of from approximately 10° C. to approximately 30° C., the lauroyl peroxide not being heated above the melting point thereof during the method.

2. Method according to claim 1, wherein production of lauroyl peroxide is carried out in the aqueous phase.

3. Method according to claim 1, wherein the method is carried out at a predetermined temperature in the range of from approximately 15° C. to approximately 20° C.

4. Method according to claim 1, wherein the alkane is selected from the group consisting of straight-chain alkanes, branched-chain alkanes, cyclic alkanes, and mixtures thereof.

5. Method according to claim 1, wherein the alkane is a $C_{5-12}$-alkane.

6. Method according to claim 1, wherein an aqueous solution of sodium hydroxide, potassium hydroxide, or mixtures thereof, is used as the inorganic base.

7. Method according to claim 1, wherein a molar excess of hydrogen peroxide above a theoretically required amount in the reaction mixture is from approximately 30% to approximately 80%.

8. Method according to claim 1, wherein a mass ratio of alkane to lauric acid chloride in the reaction mixture is in the range of from approximately 1:10 to approximately 1:1.

9. Method according to claim 1, wherein the reaction mixture comprises further components selected from the group consisting of stabilisers for the hydrogen peroxide, surfactants, alcohols, and combinations thereof.

10. Method according to claim 9, wherein ethylenediaminetetraacetic acid or salts thereof are used as the stabilisers for the hydrogen peroxide.

11. Method according to claim 1, wherein the reaction is carried out in a stirred-tank reactor.

12. Method according to claim 1, wherein the method is carried out as a batch process.

13. Method according to claim 1, said method comprising the steps of:
   i) providing an aqueous solution comprising hydrogen peroxide and an inorganic base;
   ii) adding an alkane;
   iii) adding lauric acid chloride in a temperature-controlled manner while stirring;
   iv) continuing the stirring in a temperature-controlled manner;
   v) filtering the resulting precipitate;
   vi) washing the precipitate; and
   vii) optionally drying the precipitate.

14. Method according to claim 13, wherein during at least steps ii) to iv), a predetermined temperature in the range of from approximately 10° C. to approximately 30° C. is maintained by cooling.

15. Method according to claim 13, wherein the lauroyl peroxide is not heated above the melting point thereof during the method.

16. Powdered lauroyl peroxide formed using the method claim 1, wherein the lauroyl peroxide has a $d_{90}$ value in the range of from 50 μm to 400 μm.

17. Powdered lauroyl peroxide according to claim 16, wherein the lauroyl peroxide has a $d_{50}$ value in the range of from 10 μm to 300 μm.

18. Method according to claim 5, wherein the alkane is isohexane.

19. Method according to claim 7, wherein the molar excess of hydrogen peroxide above the theoretically required amount in the reaction mixture is from approximately 50% to approximately 60%.

20. Method according to claim 8, wherein the mass ratio of alkane to lauric acid chloride in the reaction mixture is approximately 1:4.

* * * * *